United States Patent [19]

Leir

[11] Patent Number: 4,565,872
[45] Date of Patent: Jan. 21, 1986

[54] PROCESS FOR 8-CYANO-6,7-DIHYDRO-5-METHYL-1-OXO-1H,5H-BENZO[IJ]QUINOLIZINE-2-CARBOXYLIC ACIDS AND INTERMEDIATES THEREOF

[75] Inventor: Charles M. Leir, New Richmond, Wis.

[73] Assignee: Riker Laboratories, Inc., St. Paul, Minn.

[21] Appl. No.: 545,595

[22] Filed: Oct. 26, 1983

Related U.S. Application Data

[63] Continuation of Ser. No. 386,196, Jun. 7, 1982, abandoned.

[51] Int. Cl.$^4$ .......................................... C07D 215/48
[52] U.S. Cl. ...................... 546/176; 546/94; 546/165; 546/168
[58] Field of Search .......................................... 546/176

[56] References Cited

U.S. PATENT DOCUMENTS

| | | | |
|---|---|---|---|
| 3,985,882 | 10/1976 | Gerster | 424/258 |
| 4,301,288 | 11/1981 | Leir et al. | 546/94 |
| 4,301,289 | 11/1981 | Leir et al. | 546/94 |
| 4,301,291 | 11/1981 | Leir | 546/153 |
| 4,380,543 | 4/1983 | Stern | 424/258 |

FOREIGN PATENT DOCUMENTS 932241  7/1983  United Kingdom .............. 546/176

OTHER PUBLICATIONS

Badger, G., et al., *Aust. J. Chem.*, 16, 814, (1963).
March, J., *Advanced Organic Chemistry*, McGraw Hill, New York, 1968, pp. 335, 346–347 and 777–778.
Hamada, et al., *Current Abst. Chem.*, 56(580), 225385, (1975).

*Primary Examiner*—Glennon H. Hollrah
*Assistant Examiner*—D. B. Springer
*Attorney, Agent, or Firm*—Donald M. Sell; James A. Smith; Robert W. Sprague

[57] ABSTRACT

A process for preparing 8-cyano-6,7-dihydro-5-methyl-1-oxo-1H,5H-benzo[ij]quinolizine-2-carboxylic acids from substituted benzoic acids. Intermediates involved in the process are also described. 8-cyano-6,7-dihydro-5-methyl-1-oxo-1H,5H-benzo[ij]quinolizine-2-carboxylic acids are antimicrobial agents.

2 Claims, No Drawings

PROCESS FOR 8-CYANO-6,7-DIHYDRO-5-METHYL-1-OXO-1H,5H-BENZO[IJ]QUINOLIZINE-2-CARBOXYLIC ACIDS AND INTERMEDIATES THEREOF

This is a continuation of application Ser. No. 386,196 filed June 7, 1982, now abandoned.

TECHNICAL FIELD

This invention relates to a process for the synthesis of benzo[ij]quinolizines substituted at the 8-position by a cyano group. More specifically, it relates to a synthetic process for 8-cyano-6,7-dihydro-5-methyl-1-oxo-1H,5H-benzo[ij]quinolizine-2-carboxylic acids and to novel intermediates involved in the synthetic process.

BACKGROUND ART

U.S. Pat. Nos. 3,896,131 and 3,985,882 describe the synthesis of substituted benzo[ij]quinolizine-2-carboxylic acids. The synthesis of the compound 10-cyano-6,7-dihydro-5-methyl-1-oxo-1H,5H-benzo[ij]quinolizine-2-carboxylic acid is described in Example 71 of said U.S. Pat. No. 3,896,131. That synthetic process utilizes 10-amino-6,7-dihydro-5-methyl-1-oxo-1H,5H-benzo[ij]-quinolizine-2-carboxylic acid as an intermediate, which intermediate is prepared from the corresponding 10-nitro compound. The 10-nitro compound is obtained by nitration of 6,7-dihydro-5-methyl-1-oxo-1H,5H-benzo[ij]-quinolizine-2-carboxylic acid. The 10-nitro compound is the predominant isomer obtained by such nitration. Accordingly, when preparing the 8-cyano final product, it would be desirable to employ a synthetic sequence which avoids such a nitration step.

DETAILED DESCRIPTION OF THE INVENTION

The present invention provides a process for the preparation of 8-cyano-6,7-dihydro-5-methyl-1-oxo-1H,5H-benzo[ij]quinolizine-2-carboxylic acids of Formula I

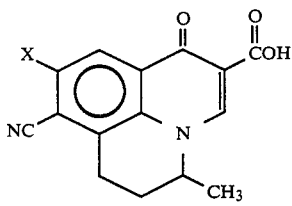

wherein:
X is hydrogen or fluorine.

The process, as diagrammed schematically in Table I below comprises the steps of:

(1) reacting a meta-aminobenzoic acid of Formula II (wherein X is hydrogen or fluorine) with crotonaldehyde in the presence of dilute aqueous acid such as hydrochloric acid, and, preferably, in the presence of a reducing-oxidizing combination such as sodium meta-nitrobenzenesulfonate and ferrous sulfate to provide the 5-carboxyquinaldine of Formula III;

(2) reacting the 5-carboxyquinaldine of Formula III to activate the carboxyl group and provide a 5-(activated-carboxyl)quinaldine of Formula IV (wherein "Q" designates a group which has activated the carboxyl group for the subsequent step);

(3) reacting the 5-(activated-carboxyl)quinaldine of Formula IV with ammonium hydroxide or ammonia gas to provide a 5-carboxamidoquinaldine of Formula V;

(4) dehydrating the carboxamido group of the 5-carboxyamidoquinaldine of Formula V to provide a 5-cyanoquinaldine of Formula VI;

(5) reducing the 5-cyanoquinaldine of Formula VI in the presence of a catalyst to provide the 5-cyanotetrahydroquinaldine of Formula VII;

(6) condensing the 5-cyanotetrahydroquinaldine of Formula VII with a diester of an alkoxymethylenemalonic acid of Formula VIIA (wherein "alk" is an alkyl group containing 1 to about 4 carbons and each $R^1$ is independently an alkyl group containing 1 to about 4 carbons or the R's together form an isopropyl radical) to provide a diester of 2-[N-(5-cyanotetrahydroquinaldinyl)]methylenemalonic acid of Formula VIII;

(7) cyclizing the diester of 2-[N-(5-cyanotetrahydroquinaldinyl)]methylenemalonic acid of Formula VIII to provide an alkyl ester of 8-cyano-6,7-dihydro-5-methyl-1-oxo-1H,5H-benzo[ij]quinolizine-2-carboxylic acid (Formula IX); and (8) deesterifying the alkyl ester of 8-cyano-6,7-dihydro-5-methyl-1-oxo-1H,5H-benzo[ij]quinolizine-2-carboxylic acid to provide said 8-cyano-6,7-dihydro-5-methyl-1-oxo-1H,5H-benzo[ij]quinolizine-2-carboxylic acid.

TABLE I

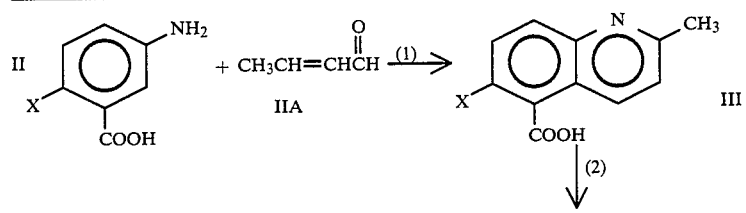

TABLE I-continued

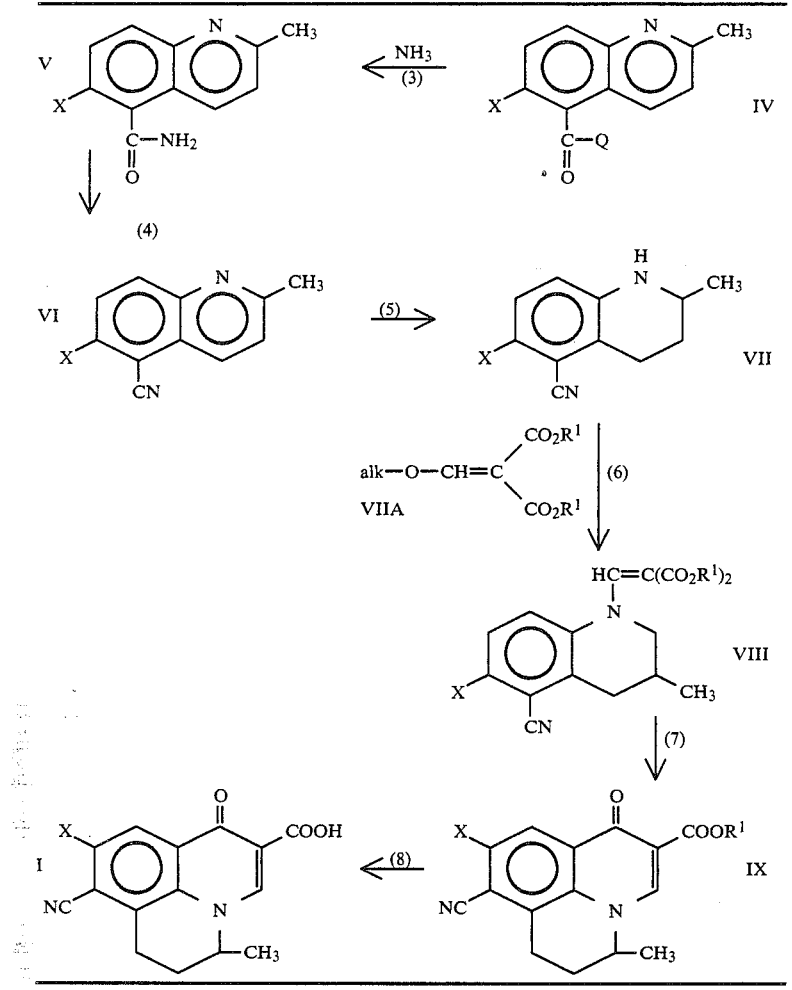

The present invention also provides novel compounds of formula X below:

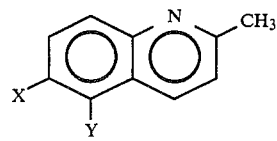

wherein:
X is hydrogen or fluorine; and
Y is cyano, carboxyl chloride, carboxamido

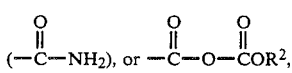

wherein $R^2$ is an alkyl group comprising 1 to 4 carbon atoms.

Formula X includes the intermediates of formulas V and VI above and many of the compounds represented by formula IV above.

The present invention further provides novel compounds of formula XI below:

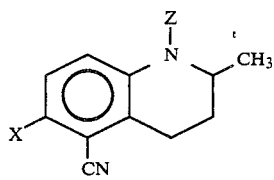

wherein:
X is hydrogen or fluorine; and
Z is hydrogen or

wherein $R^1$ is as defined previously.

Formula XI includes the intermediates of Formulas VII and VIII above.

In the first step of the reaction sequence of the present invention, 3-amino-6-fluorobenzoic acid or 3-aminobenzoic acid of formula II is reacted with crotonaldehyde of formula IIA or a precursor of crotonaldehyde which generates crotonaldehyde under the acidic conditions of the reaction. The product of step (1) is the 5-carboxyquinaldine of formula III. No detectable amount of the other possible isomer 7-carboxyquinaldine is formed.

Suitable precursors of crotonaldehyde which may be used in step 1 include acetaldehyde, acetal or paraldehyde. The reaction is conducted in the presence of a dilute aqueous acid such as sulfuric acid or hydrochloric acid, hydrochloric acid being the preferred acid. The reaction is conducted at a temperature between about 50° C. and the reflux temperature of the reaction mixture. The preferred temperature is about 95° C. It is advantageous to conduct the reaction in the presence of a reagent pair consisting of a weak oxidizing agent and a weak reducing agent. Suitable oxidizing agents include alkali metal or alkaline earth salts of the organic acid meta-nitrobenzenesulfonic acid. The sodium and potassium salts are preferred. The free acids may also be used as oxidizing agents. Suitable reducing agents include ferrous sulfate, ferric sulfate, ferric chloride, and the like. The presently preferred reagent pair is the sodium salt of m-nitrobenzenesulfonic acid as the oxidizing agent and ferrous sulfate as the reducing agent. Theoretical amounts of the oxidizing agent and reducing agent are required, i.e., at least 0.33 mole of each per mole of the aminobenzoic acid. If catalytic amounts of the reducing agent are used, the reaction proceeds, but at a slower rate. It is presently preferred to use equimolar amounts of the aminobenzoic acid and the reagent pair.

Step (2) of the reaction sequence of the present invention involves activation of the carboxyl group of the 5-carboxylquinaldine of formula III in order to permit formation of a carboxamido group in subsequent Step (3). Activation of the carboxyl group may be achieved by well-known methods such as those employed in peptide chemistry. One preferred method for activation of the carboxyl group involves reaction of the carboxylic acid group with ethyl chloroformate, N-butyl chloroformate or the like to provide a mixed anhydride. Other methods which may be used are reaction with N,N'-carbonyldiimidazole, thionyl chloride, N,N'-dicyclohexylcarbodiimide, p-nitrophenoxybenzyl chloride, or the like. When ethyl chloroformate is employed to activate the carboxyl group, the reaction is carried out at low to moderate temperatures, e.g., 0° to 20° C., in an inert aprotic solvent such as methylene chloride, chloroform, tetrahydrofuran, N,N-dimethylformamide or dichloroethane. It is preferred that an acid acceptor such as a tertiary amine (e.g., pyridine or triethylamine), an alkali metal carbonate or a bicarbonate be employed in the reaction mixture. The product of step (2) is the 5-(activated-carboxyl) quinaldine of formula IV.

In step (3) the quinaldine of Formula IV is reacted with ammonium hydroxide or ammonia gas at a low to moderate temperature, e.g., 0° to 20° C. The particular temperature selected will depend on the reactivity of the Q group. The quinaldine of formula IV may be isolated prior to conducting step (3). However, for reasons of efficiency and cost, it is preferred that the entire reaction product of step (2) be employed in step (3) without isolation of the quinaldine of Formula IV. The product of step (3) is a 5-carboxamidoquinaldine of Formula V.

The 5-carboxamidoquinaldine of Formula V is reacted in step (4) to dehydrate the carboxamido group to give the 5-cyanoquinaldine of formula VI. Dehydration may be accomplished, for example, by reaction of the 5-carboxamidoquinaldine of formula V with trifluoroacetic anhydride in the presence of a moderately strong organic base and acid acceptor such as pyridine or quinoline. It may be desirable to conduct the reaction in an inert solvent such as dichloromethane, tetrahydrofuran, 1,2-dichloroethane, or pyridine. Other suitable reagents such as thionyl chloride and phosphorus oxychloride will also dehydrate the carboxamido group to the cyano group.

The 5-cyanoquinaldine of Formula VI is reduced in step (5) to provide the tetrahydroquinaldine of Formula VII. Catalysts suitable for this reduction reaction are platinum-based and include, for example, a platinum on charcoal catalyst which is employed in an amount of about 0.5 to 1.0 g of catalyst per 20 g of the 5-cyanoquinaldine. The dry, solid compound of Formula VI is dissolved in a solvent mixture comprising a lower alkanol, such as ethanol or, preferably, isopropanol, and a weak organic acid such as acetic acid. The resulting solution is treated with a slight molar excess of a base such as ammonium or sodium acetate or triethylamine. The mixture is hydrogenated at a pressure of about 30 to 70 psi at a temperature of about 10° to 30° C. The progress of the reaction is monitored by chromatographic analysis. After completion of the reduction reaction, the catalyst and other residual solids are removed by filtration. The solvent is removed from the filtrate by evaporation, and the residual solid recovered from the filtrate is dissolved in dilute acid such as hydrochloric acid and reprecipitated by the addition of strong base such as 10 percent aqueous sodium hydroxide. The product obtained is the 5-cyanotetrahydroquinaldine of Formula VII.

In step (6) the 5-cyanotetrahydroquinaldine of Formula VII is condensed with a diester of an alkoxymethylenemalonic acid (Formula VII A) such as a dialkyl alkoxymethylenemalonate of the Formula XII

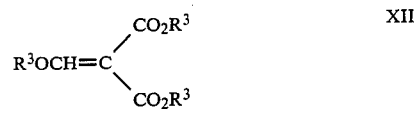

wherein each $R^3$ is independently an alkyl group containing 1 to about 4 carbons. The preferred dialkyl alkoxymethylenemalonate is diethyl ethoxymethylenemalonate since it is most readily available. Other suitable diesters of alkoxymethylenemalonic acid include N-cycloisopropylidenyl alkoxymalonates of the formula

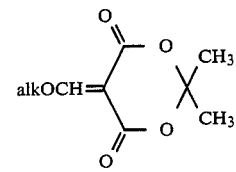

wherein alk is an alkyl group containing 1 to about 4 carbon atoms.

The condensation reaction requires heating of the reactants until the reaction is complete as determined by chromatographic analysis. The reaction may be conducted in the absence of solvent at 100° to 200° C. for about 1 to 5 hours. Alternatively, when a dialkyl alkoxymethylenemalonate is employed in the condensation reaction of step (6), the reaction is preferably conducted in the presence of an inert organic solvent which forms an azeotropic mixture with the alcohol formed upon hydrolysis of the dialkyl alkoxymethylenemalonate acid (e.g., ethanol where diethyl ethoxymethylenemalonate is employed). The reaction mixture is heated at its reflux temperature and the azeotropic mixture comprising the alcohol and the organic solvent is collected, for example, in a Dean Stark trap. Fresh organic solvent is generally added to the reaction mixture as the solvent is depleted during the distillation. Removal of the alcohol from the reaction mixture drives the condensation reaction to substantial completion and increase yields of the condensation product of Formula VIII. Preferred organic solvents for use as the entrainer have a boiling point between about 120° C. and 150° C. Specific examples of preferred organic solvents are xylene and chlorobenzene.

The condensation product of Formula VIII is preferably used directly in step (7) without further purification. However, the condensation product may optionally be purified, for example, by recrystallization prior to its employment in step (7).

In step (7), the quinaldine of Formula VIII is cyclized to form an ester of Formula IX. The cyclization step is carried out by heating the compound of Formula VIII in the presence of phosphorus oxychloride or polyphosphoric acid. The temperature of the reaction should be in the range of 100° to 140° C. if polyphosphoric acid is used, and about 107° C. (approximately the reflux temperature) if phosphorus oxychloride is used. Polyphosphoric acid may cause partial hydrolysis of the cyano group to carboxamido. However, such hydrolysis is readily reversed by a dehydration reaction using, for example, trifluoroacetic anhydride and pyridine as described above in regard to step (4). Where it is desired to avoid the additional dehydration step, the use of phosphorus oxychloride may be preferred.

In Step (8), the compound of Formula IX is deesterified by a hydrolysis reaction employing, for example, hydrochloric acid.

The compounds of Formula I prepared by the process of the present invention have been found to be exceptionally active antimicrobial agents as described in copending U.S. application Ser. No. 318,928, filed Nov. 6, 1981 and incorporated herein by reference.

The invention is further illustrated by the following non-limiting examples.

EXAMPLE 1

Synthesis of
8-Cyano-6,7-dihydro-9-fluoro-5-methyl-1-oxo-1H,5H-benzo[ij]quinolizine-2-carboxylic Acid

Part A

To a mixture of 225 ml (3.75 moles) of concentrated sulfuric acid and 225 ml (3.3 moles) of concentrated nitric acid was added 100 g (0.713 mole) of 2-fluorobenzoic acid. The temperature was maintained between 15° and 25° C. The mixture was stirred for an hour after completion of the addition, during which time the temperature rose to about 30° C. The solution was decanted into 4 liters of ice water to provide 111.1 g of white crystals of 2-fluoro-5-nitrobenzoic acid. The structural assignment was confirmed by infrared and nuclear magnetic resonance spectral analyses.

Part B

One hundred eleven g of the above 2-fluoro-5-nitrobenzoic acid (0.60 mole) was dissolved in 1 liter of ethyl acetate. To this solution was added 5 g of 5 percent palladium on charcoal. The mixture was hydrogenated on a Parr apparatus for 24 hours at 20° C. at 50 psi of hydrogen. The theoretical amount of hydrogen was absorbed. The solution was filtered and evaporated to dryness to provide a tan residue of 95.2 g of 5-amino-2-fluorobenzoic acid, a known compound.

Part C

A mixture of 95.2 g of the above 5-amino-2-fluorobenzoic acid (0.60 moles), 74.3 g (0.33 mole) of sodium meta-nitrobenzenesulfonate, 46.2 g (0.17 mole) of ferrous sulfate heptahydrate and 660 ml of 9N hydrochloric acid was heated to 90°–95° C. Crotonaldehyde (96%), 77 g (1.0 mole), was added dropwise over 2.5 hours with vigorous stirring and maintenance of temperature just below the reflux temperature. After stirring an additional half hour, the hot solution was filtered through a glass wool plug. The filtrate was cooled to 30° C., treated with decolorizing charcoal, and filtered. The clear filtrate was cooled on ice with stirring to provide a light yellow solid. The solid was separated by filtration, washed with acetone, and dried. The solid was then dissolved in 400 ml of hot water, and a solution of 50 g of sodium acetate in 100 ml of water was added thereto. The product was 58.2 g of cream crystals of 5-carboxyl-6-fluoroquinaldine. The structural assignment was confirmed by infrared and nuclear magnetic resonance spectral analyses.

Part D

A mixture of 58.2 g (0.28 mole) of the above 5-carboxyl-6-fluoroquinaldine, 200 ml of thionyl chloride and 2.5 ml of N,N-dimethylformamide was heated on a steam bath for 10 minutes. The mixture was allowed to sit at 20° C. for 0.5 hour, followed by the addition of 400 ml of diethyl ether thereto. The white solid precipitate was separated by filtration, washed with diethyl ether, and dried. This product was the acyl chloride derivative. It was added in small portions to 200 ml of cold concentrated ammonium hydroxide with rapid stirring. The mixture was stirred for 20 minutes at 20° C. The product was separated by filtration, washed with water, and dried to provide 49 g of 5-carboxamido-6-fluoroquinaldine. The structural assignment was confirmed by infrared and nuclear magnetic resonance spectral analyses.

Part E

To a mixture of 49 g (0.24 mole) of the above 5-carboxamido-6-fluoroquinaldine, 44.5 ml of pyridine and 250 ml of dichloromethane was added 37 ml of trifluoroacetic anhydride. The addition required about 6 hours and the temperature was maintained at between 24° and 27° C. The solution was stirred at 20° C. for 16 hours, and 100 ml of cold 1N sodium hydroxide solution was added. The layers were separated and the organic layer was washed with water and dried over magnesium sulfate. The organic solution was evaporated and the residue was triturated with water to provide a tan solid. The solid was separated by filtration and washed with water to provide 42.2 g of 5-cyano-6-fluoroquinaldine. The structural assignment was confirmed by infrared spectral analysis.

Part F

A solution of 42.2 g (0.23 mole) of the above 5-cyano-6-fluoroquinaldine, 150 ml of glacial acetic acid, and 150 ml of isopropyl alcohol was prepared by heating. The mixture was cooled to about 35° C. and 7.5 g of sodium acetate and 3 g of 5% platinum on carbon were added. The mixture was hydrogenated on a Parr apparatus for 72 hours at 30 psi. The theoretical amount of hydrogen was 41 psi and the actual hydrogen absorbed during the reaction was 43 psi. The catalyst was separated by filtration, and the filtrate was evaporated to provide an oil to which ice water was added. The pH of the mixture was adjusted to 8 with sodium hydroxide and sodium bicarbonate. The solid product was separated by filtration, washed with water, and dried. The product was 5-cyano-6-fluorotetrahydroquinaldine (40.2 g of cream-colored crystals). The structural assignment was confirmed by infrared spectral analysis.

Part G

A mixture of 40.2 g (0.21 mole) of the above 5-cyano-6-fluorotetrahydroquinaldine and 69 g of diethyl ethoxymethylenemalonate in 300 ml of xylene was heated at its reflux temperature for 28 hours using a Dean Stark trap to remove the xylene-ethanol azeotrope. The xylene removed was replaced with equal volumes of fresh xylene. After this reaction period, the reaction mixture was evaporated to a volume of 250 ml, followed by the addition of 500 ml of heptane. The solution was filtered, and the filtrate was treated with 350 ml of hexane. On cooling and stirring, cream crystals of the desired condensation product was obtained. The product was washed with a xylene-hexane (1:4) mixture and then with hexane to provide 58.3 g of diethyl 2-[N-(5-cyano-6-fluorotetrahydroquinaldinyl)]methylenemalonate. The structural assignment was confirmed by infrared and nuclear magnetic resonance spectral analyses.

Part H

A portion of the above diethyl 2-[N-(5-cyano-6-fluorotetrahydroquinaldinyl)]methylenemalonate (5.0 g) was combined with 15 g of polyphosphoric acid, and the mixture was heated at 140° C. for 45 minutes with stirring. The mixture was cooled, and 75 ml of water was added. The mixture was stirred for 30 minutes, and the white solid ethyl ester of 8-cyano-6,7-dihydro-9-fluoro-5-methyl-1-oxo-1H,5H-benzo[ij]quinolizine-2-carboxylic acid was obtained. Infrared and nuclear magnetic spectral analyses of this product indicated that the cyano group in the 8 position had been partially hydrolyzed back to the carboxamido group, i.e., the product obtained was a mixture of ethyl 8-cyano-6,7-dihydro-9-fluoro-5-methyl-1-oxo-1H,5H-benzo[ij]-quinolizine-2-carboxylate and ethyl 8-carboxamido-6,7-dihydro-9-fluoro-5-methyl-1-oxo-1H,5H-benzo[ij]-quinolizine-2-carboxylate.

Part I

The product mixture from part H, 4.2 g, was suspended in 250 ml of dichloromethane and 4.8 ml of pyridine. To the stirred mixture was added 4 ml of trifluoroacetic anhydride over a period of 10 minutes. The solution was stirred for three hours and washed with cold 3% sodium hydroxide solution. The solution was dried over magnesium sulfate, treated with decolorizing charcoal, and evaporated. The white residue was recrystallized from aqueous N,N-dimethylformamide to provide 2.4 g of white needles of ethyl 8-cyano-6,7-dihydro-9-fluoro-5-methyl-1-oxo-1H,5H-benzo[ij]-quinolizine-2-carboxylate, m.p. 260°–263° C. Analysis: Calculated for $C_{17}H_{15}FN_2O_3$: %C, 65.0; %H, 4.8; %N, 8.9; Found: %C, 64.4; %H, 4.8; %N, 8.8. The structural assignment was confirmed by infrared spectral analysis.

Part J

A solution of 2.0 g of the product of Part I in 35 ml hot glacial acetic acid was treated with 40 ml of 3N hydrochloric acid, and the mixture was heated at reflux temperature for one hour. The mixture was cooled and filtered, and the solid was washed with water to provide 1.7 g of 8-cyano-6,7-dihydro-9-fluoro-5-methyl-1-oxo-1H,5H-benzo[ij]quinolizine-2-carboxylic acid as a white solid, m.p. >300° C. Analysis: Calculated for $C_{15}H_{11}FN_2O_3$: %C, 62.9; %H, 3.8; %N, 9.8; Found: %C, 62.4; %H, 3.4; %N, 9.7.

EXAMPLE 2

Synthesis of 8-Cyano-6,7-dihydro-5-methyl-1-oxo-1H,5H-benzo[ij]-quinolizine-2-carboxylic Acid

Part A

A mixture of 15.1 kg (110 mole) of 3-aminobenzoic acid, 12.4 kg of sodium meta-nitrobenzenesulfonate, 7.7 kg of ferrous sulfate heptahydrate and 110 l of 9N hydrochloric acid was heated to 90°–95° C. Crotonaldehyde (91%), 12.7 kg, was added slowly, with stirring, over 6 hours while maintaining the temperature just below reflux. After stirring an additional half hour, the solution was cooled to 5° C. The solid was separated by filtration, washed with acetone and dried. The solid was dissolved in 75 l of hot water and 6 kg of sodium acetate was added. The product obtained was separated by filtration, washed with water and dried. The product was 13.58 kg (72.6 mole, 66%) crystals of 5-carboxylquinaldine. The structural assignment was confirmed by infrared and nuclear magnetic resonance spectral analyses.

Part B

To a solution of 1138 g (6.09 mole) of the above 5-carboxylquinaldine in 13 l of dichloromethane and 850 ml of triethylamine at 0° C. was added 611.4 ml (693.9 g, 6.39 mole) of ethyl chloroformate, the ethyl chloroformate being added dropwise over a period of two hours. After stirring for an additional thirty minutes, ammonia gas was bubbled through the mixture until a heavy suspension saturated with ammonia was obtained. This suspension was stirred for one hour and additional ammonia was then bubbled through the mixture until saturation again resulted. The mixture was stirred for 15 hours while allowing the temperature to rise to 20° C. The solid was separated by filtration, slurried in 2 l of 1N ammonium hydroxide and filtered. The product when dried was 706.8 g (3.8 mole, 62.4%) of 5-carboxamidoquinaldine. The structure was confirmed by nuclear magnetic resonance spectral analysis.

Part C

To a mixture of 46.5 g (0.25 mole) of the above 5-carboxamdoquinaldine, 44.5 ml of pyridine and 250 ml of dichloromethane, 37 ml (0.275 mole) of trifluoroacetic anhydride was added dropwise over five hours while maintaining the temperature between 23 and 26° C. The solution was stirred at 20° C. for 16 hours, and then enough 2N cold sodium hydroxide solution was added until the pH of the solution reached 8. The layers were separated and the organic layer was washed with water and dried. The organic solution was then evaporated, and the residue was triturated with water to provide a tan solid. The solid was separated by filtration and washed with water to provide 36.8 g (87.7%) of 5-cyanoquinaldine. The structural assignment was confirmed by nuclear magnetic resonance spectral analysis.

Part D

A solution of 52.1 g (3.12 mole) of the above 5-cyanoquinaldine and 1000 ml of glacial acetic acid and 1000 ml of isopropyl alcohol was prepared by heating. The mixture was cooled to about 35° C., and 40 g of ammonium acetate and 40 g of 5% platinum on carbon were added. The mixture was hydrogenated on a Paar apparatus for 5 days at 50 psi. The catalyst was separated by filtration and the filtrate was evaporated to provide an oil. Ice water was then added, and the pH of the mixture was adjusted to 8 with sodium hydroxide. The solid product was separated by filtration, washed with water, and dried. The product was 5-cyanotetrahydroquinaldine (355 g, 66.2%). The structural assignment was confirmed by nuclear magnetic resonance spectral analysis.

Part E

A mixture of 352 g (2.06 mole) of the above 5-cyanotetrahydroquinaldine and 891 g (4.12 mole) of diethyl ethoxymethylenemalonate in 2.5 l of xylene was heated at its reflux temperature for 28 hours using a Dean Stark trap to remove the xylene-ethanol azeotrope. The xylene removed was replaced with equal volumes of fresh xylene. After this reaction period the reaction mixture was evaporated to a volume of 250 ml. To this solution was added 1 liter of hexane. The solution was filtered and the filtrate was treated with 350 ml of hexane. On cooling and stirring, crystals of the desired condensation product were obtained. The product was separated by filtration to provide 568 g (1.66 mole, 80.5%) of diethyl 2-[N-(5-cyanotetrahydroquinaldinyl)-]methylenemalonate. The structural assignment was confirmed by infrared and nuclear magnetic resonance spectral analyses.

Part F

A mixture of 565 g (1.65 mole) of the above diethyl 2-[N-(5-cyanotetrahydroquinaldinyl)]methylenemalonate and 1000 ml of phosphorus oxychloride was heated at reflux for four hours. The mixture was purged with nitrogen gas until the temperature dropped to about 40° C. The mixture was then poured slowly and carefully into an ice-water mixture. The mixture was boiled for about four hours, and then cooled. A pink product was isolated by filtration and boiled for four hours in N,N-dimethylformamide. The solution was cooled and the product isolated by filtration. The product was washed sequentially with N,N-dimethylformamide, water and methanol and was then dried in vacuo to provide 306.2 g (1.14 mole, 69.2%) of 8-cyano-6,7-dihydro-5-methyl-1-oxo-1H,5H-benzo[ij]quinolizine-2-carboxylic acid as a light pink solid. Further purification was conducted by slurrying the solid in 7 l of 3N hydrochloric acid, filtering the mixture and then washing the solid sequentially with 3N hydrochloric acid and water. The solid was then dissolved in a solution containing 2 l acetonitrile and 400 ml of 3N hydrochloric acid, dissolution being accomplished with heating. The solid which formed on cooling of the solution was recovered by filtration and was then washed with 3N hydrochloric acid and water and dried. Analysis of this product was: Calculated for $C_{15}H_{12}N_2O_3$: %C, 67.15; %H, 4.51; %N, 10.44; Found: %C, 67.3; %H, 4.3; %N, 10.4. The structural assignment was confirmed by nuclear magnetic resonance spectral analysis.

EXAMPLE 3

Preparation of 5-Cyanoquinaldine (Step 5) by Alternative Procedure

To 18.6 g (0.10 mole) of solid 5-carboxamidoquinaldine was added 18.6 ml (0.20 mole) of phosphorus oxychloride. An additional 10 ml portion of phosphorus oxychloride was added and the mixture was heated. After about one hour the mixture could be stirred. After three hours, the mixture was cooled and then poured into an ice-water mixture. The solution was adjusted to pH 8 by the addition of 10% aqueous sodium hydroxide solution. The solution was extracted with dichloromethane, the extracts then being evaporated to provide 14.7 g (0.0875 mole, 87.5%) of solid 5-cyanoquinaldine. The structural assignment was confirmed by nuclear spectral analysis.

EXAMPLE 4

Preparation of 5-Carboxylquinaldine (Step 1) by Alternative Procedure

A suspension of 1.783 kg (13 mole) of 3-aminobenzoic acid in 7.475 l of water and 8.125 l of concentrated hydrochloric acid was heated at reflux while adding slowly 1.0 l (1.026 kg, 13.5 mole) of 91.5% aqueous crotonaldehyde. The addition required 8 hours, and refluxing was continued for an additional one hour. After cooling, the solid precipitate was separated by filtration, washed with acetone, and dissolved in 13 l of boiling water, 1175 g (14.33 mole) of sodium hydroxide then being added to the resulting mixture. After cooling, the precipitate was isolated by filtration and washed with water to provide 1138 g (6.09 mole, 46.8%) of 5-carboxylquinaldine. The structure was confirmed by nuclear magnetic resonace spectral analysis (known compound).

A repeat of the above procedure provided 1046.7 g (5.6 mole, 43.1%).

What is claimed is:

1. A compound selected from the group consisting of 5-cyanoquinaldine and 5-cyano-6-fluoroquinaldine.

2. The compound 5-cyano-6-fluoroquinadline according to claim 1.

* * * * *